US009074982B2

(12) United States Patent
Ramírez Salgado et al.

(10) Patent No.: US 9,074,982 B2
(45) Date of Patent: Jul. 7, 2015

(54) MODULAR DEVICE TO MEASURE IONIC, ELECTRONIC AND MIXED CONDUCTIVITY IN POLYMERIC AND CERAMIC MEMBRANES

(75) Inventors: Joel Ramírez Salgado, Mexico City (MX); Marco Antonio Domínguez Aguilar, Mexico City (MX); Arquimides Estrada Martínez, Mexico City (MX); Marcelo Lozada Y Cassou, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 160 days.

(21) Appl. No.: 13/598,678

(22) Filed: Aug. 30, 2012

(65) Prior Publication Data

US 2013/0057295 A1    Mar. 7, 2013

(30) Foreign Application Priority Data

Aug. 31, 2011    (MX) .................... MX/a/2011/009115

(51) Int. Cl.
*G01N 27/02* (2006.01)

(52) U.S. Cl.
CPC ....................................... *G01N 27/02* (2013.01)

(58) Field of Classification Search
CPC ..... Y02E 60/521; Y02E 60/50; Y02E 60/525; Y02E 60/527; H01M 4/8605; H01M 4/926; H01M 4/134; H01M 2008/1095; H01M 8/1004; H01M 8/881; H01M 8/1053; H01M 8/00; H01M 8/02; H01M 8/04; H01M 8/10; G01R 27/08

USPC ...................... 324/439, 71.1, 71.3, 71.4, 444, 324/447–450, 691–693; 73/53, 61.71, 73/61.73, 41, 865, 861.41, 865.5; 702/26, 702/29; 422/80, 82, 78, 90, 93, 68; 429/42, 429/43, 101, 429, 431, 468, 465, 471, 480, 429/502, 506, 515, 523

See application file for complete search history.

(56) References Cited

U.S. PATENT DOCUMENTS

| 2,422,873 | A | | 6/1947 | Wolfner | |
|---|---|---|---|---|---|
| 3,407,249 | A | * | 10/1968 | Landi | ............... 264/49 |
| 4,118,549 | A | | 10/1978 | Liang et al. | |
| 4,562,123 | A | * | 12/1985 | Shimizu et al. | ............... 429/462 |
| 4,871,427 | A | | 10/1989 | Kolesar, Jr. | |
| 6,183,695 | B1 | * | 2/2001 | Godec et al. | .................... 422/79 |
| 6,228,325 | B1 | | 5/2001 | Godec et al. | |
| 6,458,479 | B1 | * | 10/2002 | Ren et al. | ...................... 429/480 |
| 6,498,121 | B1 | * | 12/2002 | Gorer | ........................... 502/325 |

(Continued)

OTHER PUBLICATIONS

U.S. Appl. No. 13/186,957, filed Jul. 2011, Goto et al.*

(Continued)

*Primary Examiner* — Arleen M Vazquez
*Assistant Examiner* — Neel Shah
(74) *Attorney, Agent, or Firm* — Roylance, Abrams, Berdo & Goodman, L.L.P.

(57) ABSTRACT

This invention consists in a device and a method to determine the ionic, electronic and mixed (electronic-ionic) conductivity in polymer, ceramic and composite (polymeric-ceramic) membranes. The invention device may work from room temperature to 300° C. and the method includes the collection and analysis of electrochemical impedance spectra during cell operation.

18 Claims, 8 Drawing Sheets

(56) References Cited

U.S. PATENT DOCUMENTS

| | | | |
|---|---|---|---|
| 2002/0015875 A1* | 2/2002 | Kim | 429/33 |
| 2003/0076110 A1* | 4/2003 | Wang et al. | 324/444 |
| 2005/0260471 A1* | 11/2005 | Logan et al. | 429/23 |
| 2006/0240300 A1* | 10/2006 | Thompson et al. | 429/26 |
| 2007/0218327 A1* | 9/2007 | Ishikawa et al. | 429/22 |
| 2007/0238000 A1* | 10/2007 | Koyama et al. | 429/33 |
| 2009/0068544 A1* | 3/2009 | Ragsdale et al. | 429/43 |
| 2009/0092881 A1 | 4/2009 | Ito et al. | |
| 2010/0109651 A1* | 5/2010 | Tolmachev et al. | 324/149 |

OTHER PUBLICATIONS

Roziere, J. et al., Conductivity characterisation of proton conducting membranes, CNRS, 2007.

DuPont Fuel Cells, DuPont Nafion PFSA Membranes, www.fuelcells.dupont.com, 2009.

Gode, P. et al., Influence of the composition on the structure and electrochemical characteristics of the PEFC cathode, Electrochimica Acta 48 (2003) 4175-4187.

Ramirez-Salgado, J., Study of basic biopolymer as proton membrane for fuel cell systems, Electrochimica Acta 52 (2007) 3766-3778.

Zawodzinski, T. et al., Determination of water diffusion coefficients in periluorosulfonate ionomeric membranes, J. Phys. Chem. 1991, 95, 6040-6044.

Smart, L. et al., Solid State Chemistry: An Introduction, Taylor & Francis, 2005.

Gutierrez, M. et al., Thin Film Surface Resistivity, 2002.

Heiman, D., van der Pauw Hall Effect Measurement, 2009.

* cited by examiner

MODULAR DEVICE TO MEASURE IONIC, ELECTRONIC AND MIXED CONDUCTIVITY IN POLYMERIC AND CERAMIC MEMBRANES

CROSS-REFERENCE TO RELATED APPLICATION

This application claims the benefit under 35 U.S.C. §119 of Mexican Patent Application No. MX/a/2011/009115, filed Aug. 31, 2011, which is hereby incorporated by reference in its entirety.

FIELD OF THE INVENTION

The actual invention is a useful device to detect ionic, electronic and mixed conductivity in polymeric, ceramic and composite membranes. The main objective of this invention is to simulate real operating conditions at work, such as those present in fuel cells, batteries, electrochemical sensors and pseudo-capacitors, where electrical conductivity plays an important role in the operation of the systems. The modular device permits the work of two electrodes, either blocking or non-blocking electrodes and with one or two different atmospheres (gases), or one or two different liquids in each compartment divided by the same membrane.

The device of the invention is a conductivity cell composed of two inlets and two outlets to convey gas or liquid, a heating system formed by electric resistance, and an opening for the temperature control thermocouple. The cell is fabricated in aluminum to have a high corrosion resistance and an improved heat transfer. The two compartments are divided by the same membrane, which is isolated from aluminum by silicon or glass seals as needed and depending on use. This array allows the cell to stay in direct contact with gases or liquids and this way monitor the charge carriers throughout the membrane. As a result of cell modularity, it is possible to carry out interfacial studies of electrochemistry type by means of the cell connection to a potentiostat-galvanostat or to an impedance spectrometer.

BACKGROUND OF THE INVENTION

The electric conductivity is a material's ability of allowing the flow of electric current through itself. It is also defined as a natural property to measure the capacity of providing electrons (or electronic holes as is the case of semiconductors), ions or both types of particles or charge carriers that can flow through a material.

An electrolyte is a substance composed of ions; there exist different types of electrolytes such as liquids, solids and gases (plasma: highly ionized gas). Solid electrolytes can be made of a polymeric, ceramic and composite (polymeric-ceramic) material. A family of materials in constant growth is that of ionic solids, in which certain ions exhibit a quick transport. These materials are commonly named as fast ion conductors (FICs). In certain cases, the rapid transport of ions is accompanied by a considerable increase in electronic conduction (mixed conductivity).

There is a large interest in the science and technology of FIC due to their potential to be used as electrodes and electrolytes in conversion devices of electrochemical energy. These solid electrolytes have other applications in industry, including sensors to detect insulin and oxygen, the latter being used in automobiles. Other applications involve power systems such as electrochemical super-capacitors, fuel cells, batteries and accumulators such as those based on lithium.

In order for a solid to have fast ion conduction it must fulfill the following criteria [West A. R., Solid State Chemistry and Its Applications, John Wiley & Sons Essex, 1984]:
1. Have a high concentration of charge carriers or potential charge carriers.
2. Have a high concentration of vacancies for ion movement or interstitial sites.
3. Have a low activation energy for ion movement.
4. Have the presence of a set of energetically equivalent sites partially occupied by other mobile ions.

FICs are not a new discovery. In 1914, Tubandt and Lorenz observed this behavior in certain silver compounds. These researchers discovered, for example, that ionic conductivity of AgI before fusion was approximately 20% higher than that of the melted solid. The FICs were also observed in other two iodine compounds and AgSI. As it was mentioned in FICs one of the groups of ions, cations or anions is free to move. That group is called sub-reticle and generally it is in a melted state. That model was proposed by Strok in 1936 based on structural and thermodynamic data of AgI. In most of the FICs, entropy for transition to the FIC state is higher than that of a non-conducting FIC. For example, in the AgI, the transition entropy from form b (non-conducting) to a (fast conducting) form at 420 K is 14.7 $JK^{-1}mol^{-1}$, while the fusion entropy at 861 K is hardly of 11 $JK^{-1}mol^{-1}$.

The special electric properties of $\alpha$-AgI led to an unavoidable search for other solids that exhibited a high ionic conductivity, mainly at temperatures lower than 420 K. The most successful solid at present, despite the existence of others, involved the partial change of silver by rubidium to form an $RbAg_4I_5$ compound. This compound has an ionic conductivity of 2,500 $Sm^{-1}$ at room temperature, which is higher than that of a NaCl sodium that has an activation energy of just 0.07 eV ($1.12 \times 10^{-20}$ J). The crystalline structure is different from that of $\alpha$-AgI, but similarly, the ions of $Rb^+$ and $I^-$ form a rigid reticle, while those of $Ag^+$ are randomly distributed in a grid of tetrahedral sites in which they can move [Smart, L.; Moore, E., Solid State Chemistry: An Introduction. Chapman & Hall, Londres, 1993].

To be useful as a solid electrolyte in a battery, an ionic conductor not only must have a high electrical conductivity but also negligible electronic conductivity to avoid the battery short circuiting. Electrons have to cross the external circuit where they can be used to make a useful work. The electronic conductivity of $RbAg_4I_5$ is considerably small ($10^{-7} Sm^{-1}$) so that it has been used as a solid electrolyte in batteries with electrodes made of Ag and $RbI_2$. Such cells operate in a wide range of temperatures 217-473 K (−55 to 220° C.), require a long time to store energy and provide a high mechanical resistance.

The most promising application of FICs is in solid state batteries, where two types of batteries exist:
1. Small primary cells; they must have a long lasting life and must not be discharged during this period
2. Rechargeable secondary batteries; they are used when a high density of energy is the selection criterion.

The batteries of the first type find application as miniature cells; they operate at room temperature and have a long lasting life in the order of years instead of a high density of energy or a high outlet voltage. They are used in watch clocks and photographic machines, pacemaker and military applications. The secondary batteries manage a lithium anode, lithium iodine as electrolyte and the complex as cathode:

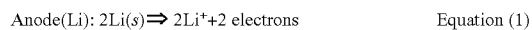

Anode(Li): $2Li(s) \Rightarrow 2Li^+ + 2$ electrons   Equation (1)

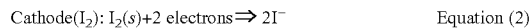

Cathode($I_2$): $I_2(s) + 2$ electrons $\Rightarrow 2I^-$   Equation (2)

Total: $2Li(s)+I_2(s) \Leftrightarrow 2LiI$      Equation (3)

As LiI has vacancies in the reticle and as a result of the small size of Li+ cations, these are able to migrate through the solid electrolyte whereas electrons flow through the circuit.

There are several devices and equipment suitable to measure the conductivity of solid electrolytes but most of them have their application in liquid solutions. For solid systems, devices based on the Van der Pauw's method are used (FIG. 1).

Other equipment in use for the measurement of resistivity is that of Van der Pauw, in which the sample used can have an arbitrary form (though homogeneous in composition and thickness) and electric contacts can be taken on any point of its profile. The only restriction is that the sample must be thin. FIG. 2 shows a diagram corresponding to the setup of equipment.

At first, the potential difference between C and D, $V_{CD}=V_D-V_C$ is measured by passing an electric current between A and B to calculate R1:

$R1=V_{CD}/I_{AB}$      Equation (4)

The voltage difference between A and D, $V_{DA}=V_A-V_D$ is measured by passing an electric current between B and C to calculate R2:

$R2=V_{AD}/I_{BC}$      Equation (5)

In agreement with Van der Pauw's method, resistivity ρ is given by the expression:

$$\rho \approx \frac{\pi * d}{\text{Ln}(2)} * \frac{R_1 + R_2}{2} \quad \text{Equation (6)}$$

where d is the sample thickness.
$R_1$ is the vertical resistance
$R_2$ is the horizontal resistance When resistivity measurements are performed on samples with a form of rectangular parallelogram, the four point method is used (FIG. 2). Current is introduced in two parallel faces of the sample, whilst voltage is measured in two intermediate points within this distance, thereby avoiding a voltage loss in the points of electric contact (impedance at voltmeter entrance must be much higher than that of the resistance between voltage contacts).

A sample resistivity is given by expression:

$\rho=VA/IL$      Equation (7)

where V is the voltage, I is the current, A is the sample section and L is the distance between the voltage contacts:

Nevertheless, the specific determination of ionic carrier is not identified by means of this equipment so that the application of blocking or selective electrodes (that permit the pass of electrons or ions only) is widely useful in determining carrier type (For example, if a solid electrolyte transports two types of ion carriers such as "A" and "B" then it is possible to have electrodes that permit only the pass of "A" or "B" ion to be determined but not both at the same time).

With the aim of having a cell that measures not only the general electric resistance but also a specific resistivity (or conductivity), it is possible to know from it what type of carrier is having effect on work. The present conductivity cell has been therefore developed with blocking and selective electrodes.

In the reference *J. Phys. Chem.* 1991, 95, 6040-6044, an open cell is shown in a two-electrode set up with charge carriers that flow on the surface. In this cell, it is not possible to control pressure and relative humidity of input gas to the system, so that membrane was hydrated before placing it in the conductivity cell to obtain values by means of electrochemical impedance.

In the reference *Electrochimica Acta* 48 (2003) 4175-4187, the Van der Pauw's method of four electrodes is used, in which iterations were carried out on equations to obtain a conductivity value, likewise charge carriers flow on the membrane surface.

In US 2010/0109651 A1, a conductivity cell can work with two or four electrodes, but only with one atmosphere, and conductivity measurement is performed on surface and not through it.

U.S. Pat. No. 4,118,549 describes a solid state cell to measure conductivity of the battery type composed of two electrodes, which does not permit gas entrance. Electric charge transportation is through membrane but it does not have a heating system or pressure control.

In U.S. Pat. No. 4,871,427, the cell described consists of two electrodes, which can handle liquids only but not gases.

In U.S. Pat. No. 6,228,325, a cell to measure the quantity of carbon by means of electric conductivity is reported. Despite having generally the same principle of operation as the invention cell, this application is different and more specific for this case.

SUMMARY OF THE INVENTION

The present invention is directed to a device and method for measuring ionic, electronic and mixed conductivity of materials. The materials can be polymeric, ceramic or composites in the form of membranes or thin films. The device is constructed to simulate working conditions such as those used in fuel cells, batteries, pseudo-capacitors and sensors.

The main difference of the conductivity cell used in the present invention is the capacity to work in a wide range of temperature, from room temperature and up to 300° C., by means of electric resistance. As it is known, the electronic conductivity decreases as temperature increases but the ionic conductivity increases with temperature. On the other hand, this cell has two compartments separated by the same membrane to be evaluated, which allows the use of different gases such as oxygen in one side and hydrogen in the other (for example, fuel cell application). Alternatively, compartments can be filled with water or any aqueous solution and the other by an aprotic solution. This cell can stand a maximum pressure of 6 atmospheres, which permits changes in gas pressure, or if a certain gas under study is dissolved into an inert gas. For example, the change of partial pressure of oxygen in nitrogen to study the effect on ionic conductivity by carriers (or vacancies), or changing the partial pressure of hydrogen and observing the effect on the protonic membrane.

Another substantial advance of this cell is the versatility to interchange charge collecting electrodes that are in direct contact with the membrane, on which it can be designed metallic deposits on a graphite mesh that will serve equally. These deposits will permit electrodes that are selective, for example, deposits can be made on platinum or palladium on graphite mesh. Platinum is a good catalyst to divide hydrogen in its ionic form, which monitors the charge flow of hydrogen ion within a membrane with charge carriers of the protonic type.

The state of the art in the conductivity cell design is not extensive. For example, some different devices may be described in various patents or journals. However, charge carriers in any such devices flow on the membrane surface and not through it. In the present invention, charge carriers travel through the membrane and not on it, which avoids ohmic loss and consequently a better conductivity is obtained. Several authors and inventors mentioned that when four electrodes and charge carriers flow on the membrane and not through it, ohmic losses are avoided to produce an improvement in conductivity. However, the device of the present invention simulated the best working conditions, be it in fuel cells, electrochemical sensors, pseudo-capacitors or electrophoresis systems. In addition, it is well known that the surface at microscopic level in polymer, ceramic and composite membranes is largely different to that one in the membrane bulk, which can modify the data obtained to be higher in the superficial mode than in the transversal mode as exemplified below.

The device of the present invention includes two plates coupled together by screws or other coupling members. The plates are made of a heat conducting material, such as a suitable metal. In one embodiment, the plates are made of aluminum and are provided with a heat source. The plates can have two spaced-apart holes or cavities that receive an electric resistance heating member. At least one of the plates has a thermocouple to control the temperature of the plates. The thermocouple can be received in a recess formed in one of the plates.

The membrane being tested is captured between the plates. A suitable gas or liquid is passed through the device by an inlet or outlet provided in each of the plates.

The membrane to be tested is supported by a mesh such as a graphite mesh. Two graphite mesh supports are provided to support the membrane therebetween with the flow path of the device. The graphite mesh supports include a supporting frame made of a heat resistant plastic material forming a seal. The graphite mesh supports are captured between a pair of electrodes or electric current collectors that are connected to an impedance measuring device. The electrodes are captured between the plates and separated from the plates by a seal made of a fiberglass material or borosilicate seal.

The method of the invention, positions the membrane to be tested between the two graphite mesh supports that are positioned between the two electrodes. The assembly is clamped between the plates and a gas or liquid is passed through the resulting assembly. The impedance is measured between the electrodes to measure the ionic or electronic conductivity.

The gas or liquid is supplied to the device from a suitable source. The medium can be a suitable gas or liquid medium as known in the art. The medium can be an aqueous medium or a gaseous medium such as water vapor. The conductivity to be measured can be electronic conductivity and ionic conductivity such as cationic conductivity, anionic conductivity or combinations thereof. The conductivity can be conductivity of various ions such as, for example, $H^+$, $Ag^+$, $Li^+$, $Cd^{2+}$, and $Hg^{2+}$. The conductivity can be AC conductivity or DC conductivity. The anionic conductivity can be, for example, $O^{2-}$.

The features of the invention will become apparent from the following detailed description of the invention which disclose various embodiments of the invention.

DETAILED DESCRIPTION OF THE INVENTION

The new structure of the invention device can be adapted for measurements of ionic, electronic or mixed conductivity type of polymer membranes, ceramics and composites, using a single modular design which allows the use of different types of electrodes blockers, non-blockers or selective.

The present invention device works in two-electrode mode but it permits the inclusion of ohmic losses that occurred in real systems, which may provide a more realistic idea of the electric conductivity behavior of membrane. The membrane is not only subjected to an AC voltage but also to physical stresses of mechanical tension derived from the pressure system. The actual cell makes use of two different gases in two compartments, respectively, such as hydrogen and oxygen at different pressures, which can be evaluated to observe the effect on the electric conductivity of membrane.

On the other hand, it is possible to obtain data of electric conductivity from the charge carriers in the sample's bulk and not only on its surface.

Figure 1:
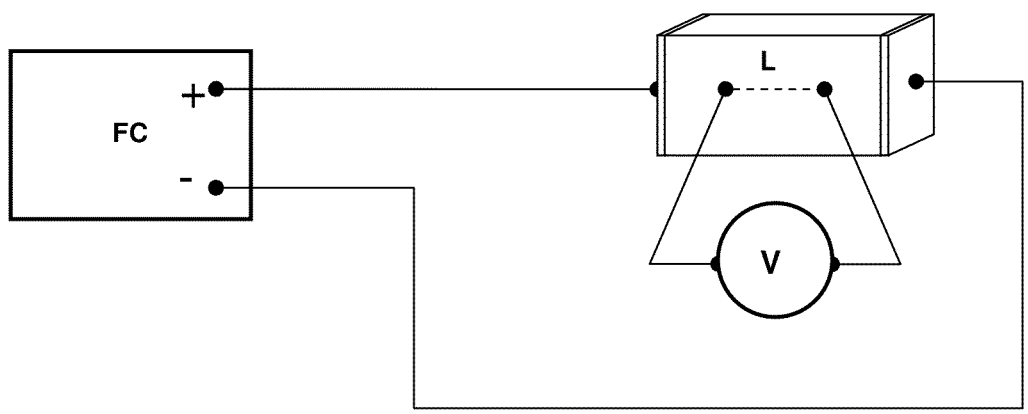
FIG. 1 shows a diagram of the conventional method for measuring electrical conductivity known as 4-point method.
where:
FC=source of direct electric current
L=distance between electrodes
V=voltage.
Figure 2:
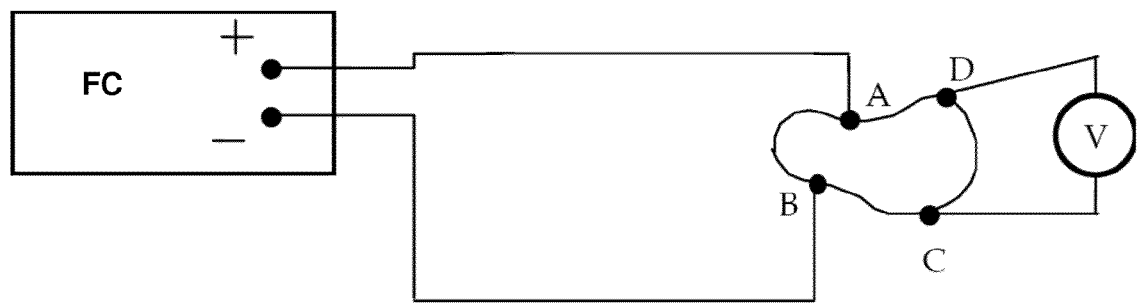
FIG. 2 shows a diagram of the Van der Pauw method.
where:
FC=source of direct electric current
V=voltage
A=point A
B=point B
C=point C
D=point D
Figure 3:
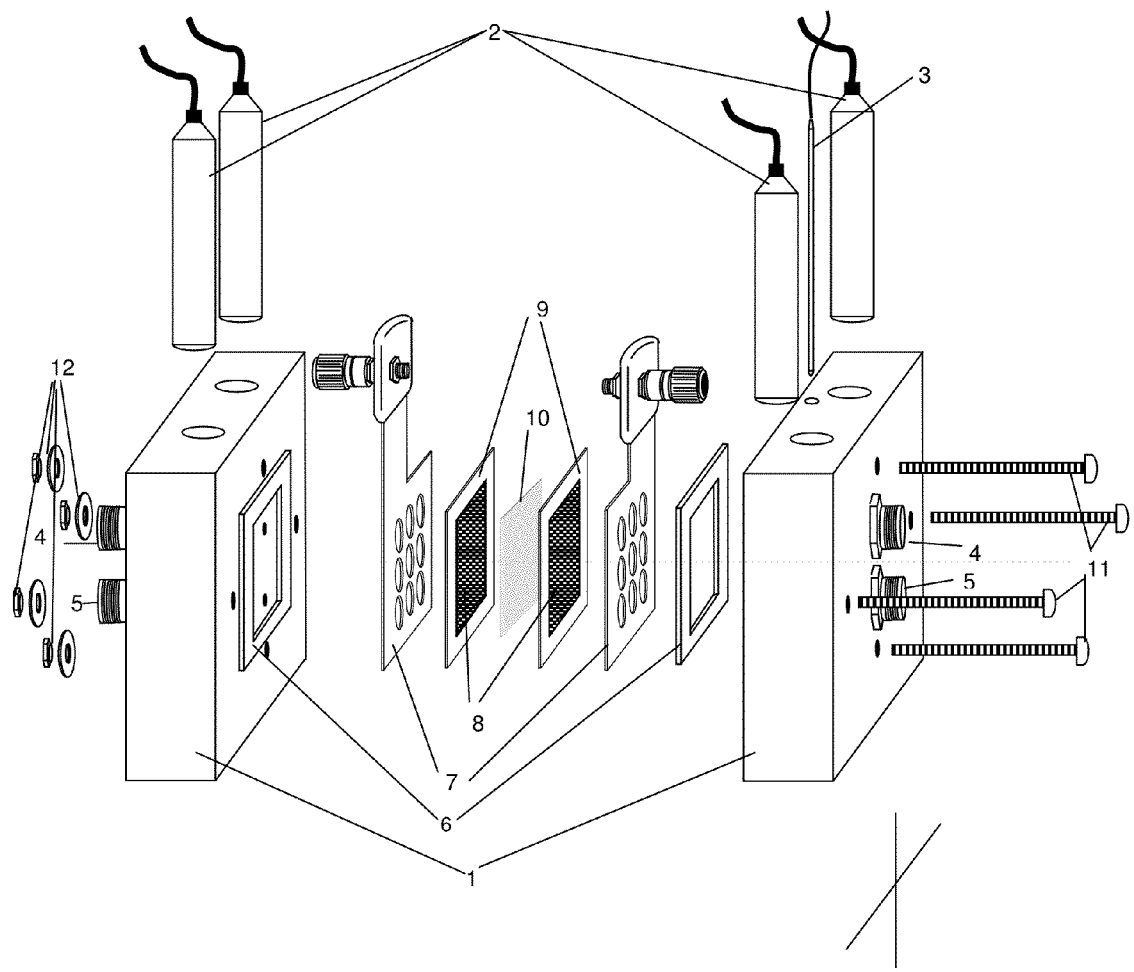
FIG. 3 shows a view in perspective of the invention cell, where symmetric modules are observed along with the heating system composed of electric resistance devices and a thermocouple. Electric current collectors have been provided with holes to allow a better flow of reactant gas.
where:
1=two aluminum plates
2=electric heater
3=thermocouple
4=input gas or fluid
5=output gas or fluid
6=silicon frames or borosilicate glass type material
7=electric current collectors
8=mesh of graphite or platinum
9=plastic insulation
10=membrane to be evaluated
11=screws
12=nuts and washers

More specifically, the apparatus of the invention is formed by two pieces of aluminum material (1), die-cut to receive the electric resistor heating devices (2) to allow heating of the cell and an input for a thermocouple (3), which allows the control and temperature measurement. As shown in FIG. 3, the plates 1 have a top side with bores formed therein to receive the heating elements 2 and the thermocouple 3. Two aligned apertures in each of the plates 1 provide an input and output 4 and 5, respectively, for a gas or liquid. The faces of the plates 1 that face towards the membrane 10 (polymer, ceramics and composites) are flat and mirror polished. The plates 1 are provided with seals 6 in the form of silicone material frames or rubber for withstanding temperatures up to 150° C. The seals 6 can be made from a glass fiber material or borosilicate glass type, or some other material that will withstand temperature changes and temperatures up to 300° C.

The device has two electric current collectors (7) or electrodes mainly made of stainless steel but can be made of other metals or metal-coated corrosion-resistant material, such as, for example, gold, (resistant corrosion by hydrogen) depending on the gases or liquids to be handled. The device has in turn, a highly conductive graphite mesh (8) which is in direct contact with the membrane 10 to be evaluated.

The mesh graphite 8 acts as a blocking electrode ion and only allows the passage of the electron flow (pseudocapacitors). For example by depositing platinum on the mesh graphite, this allows the passage protons (selective electrodes, together with the membrane) making it possible to value the charge carrier mobility and determine directly through the membrane 10 in question. The graphite mesh 8 can be replaced by one of platinum or gold directly. Also, it may be done with another kind of deposit such as ionic salts (e.g. lithium salt) which will enhance the selectivity of charge carrier, in terms of the function of membrane type (e.g. lithium batteries or electrochemical sensors), or the blockade of some other charge carrier different from those being evaluated and that could interfere in the measurement. On the edge of the graphite mesh 8, the selective or the blocker electrode (as applicable), is placed a silicone-based plastic insulator (9) with high electrical and thermal resistance, which holds and fixes the graphite mesh 8 that has platinum deposit or any other deposit as the case study requires. The plastic insulation 9 prevents direct contact of current collectors 7 with the membrane 10 and each other. Finally, in the middle is placed the polymer, ceramic or composite membrane 10 to be evaluated.

All modules are placed and aligned as shown in FIG. 3. The studs or screws (11), in addition to holding the constituent parts of the conductivity measuring device, allows an accurate alignment of the device components. Device modules are placed in layers and fastened by nuts and washers (12) by applying a measured pressure to prevent gas leaks from the conductivity measurement system.

Figure 4:
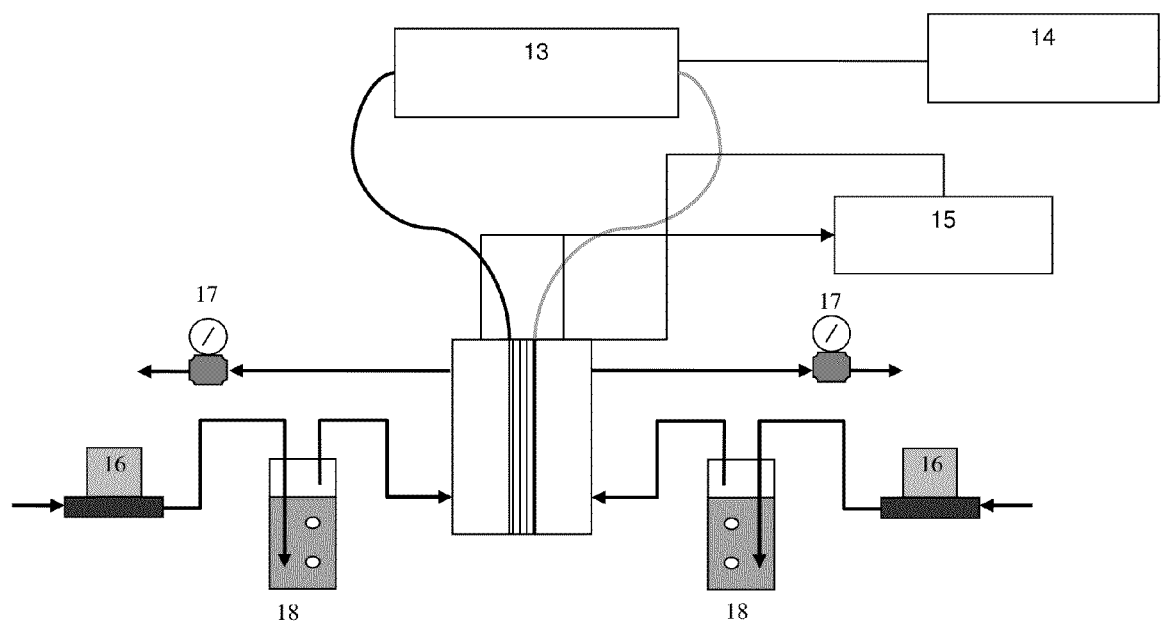
FIG. 4 shows schematically the arrangement of two points to obtain the impedance spectra from which the ionic membrane conductivity is calculated.
where:
13=impedance spectrometer
14=computer
15=temperature controller
16=flow controllers
17=pressure controllers
18=humidifier FIG. 5 exemplifies an impedance spectrum, whose analysis provides the membrane ionic conductivity made of a sulfonated tetrafluoroethylene copolymer.

Once having assembled the whole device, this is connected to an impedance spectrometer (13) shown in FIG. 4 and to a computer (14) for control. In the embodiment shown, the electric current collectors 7 functioning as electrodes are connected to impedance spectrometer 13. The electrical resistance device 2 and thermocouple 3 are connected to a temperature controller (15). The inputs 4 and outputs 5 of gases or liquids are provided with flow (16) and pressure (17) controllers. In the case of gases, a humidifier (18) is required to hydrate them. FIG. 4 shows the invention device and auxiliary parts. The gases or liquids introduced to each side of the membrane 10 being tested are generally different to enable the measurement of the conductivity of the membrane. The gases and liquids can be selected from suitable gases and liquids as known by those skilled in the art of conductivity measurements.

The ionic conductivity of a specific material is strictly related to the ohmic loss associated with the membrane during operation. In many cases, the key in research for the development of membranes is in improving the ionic transport in the direction of having a minimum drop potential, particularly in fuel cells operating at high current densities, or in electrochemical sensors, batteries or super-capacitors (pseudo-capacitors) to be evaluated under similar conditions to their work environment.

Operation of the Device

In view of the discussion of the figures, it is observed that the device is composed of different pieces with a square profile or other common profile. The cell of the invention is constructed in its outer modules with aluminum metal with two holes on each side for the input and output of reactant or inert gases or liquids. The faces looking at the membrane must be mirror polished, which allows a better sealing of the system.

The metal plates contain four holes to align the modules and fix them with screws to prevent leaks and displacements. Two square seals made of silicone or silicone mixture of glass fiber or glass for temperatures above 130° C. with dimensions including the input and output of gases having a thickness of 3 mm. Current collectors with a nearly square profile at the ends are made of stainless steel with a gold coating. Its dimensions match exactly with the dimensions of joints and a thickness of 1 mm. Gas diffusers are made of paper or porous graphite mesh, or a mesh of platinum, or any other conductive material. Similarly, an inert material and conductor such as graphite or platinum are coated with a material that is dependent on the charge carriers in the membrane to be analyzed. These materials should join together by an adhesive of polymeric type that withstands high temperatures and provides electric current insulation. This adhesive must withstand the temperature range of operation with the same dimensions of those of the joints and collecting boards.

The system operation to determine the electric conductivity is based on the following methodology.

The membrane is placed inside the conductivity cell as shown in FIG. 3.

The relevant connections are made according to the scheme of FIG. 4.

Membrane can be hydrated at one of the different relative humidity values or by using different atmospheres depending on the ionic carriers to evaluate.

The supply of gases or liquids is opened; fluid is permitted to flow for about 20 minutes for purging the gases present in the cell.

The operating temperature of the system is selected and regulated by means of a temperature controller.

The operating pressure of the system is set.

The gas flow in the system is adjusted.

Conductivity is evaluated by impedance spectroscopy.

Figure 5:
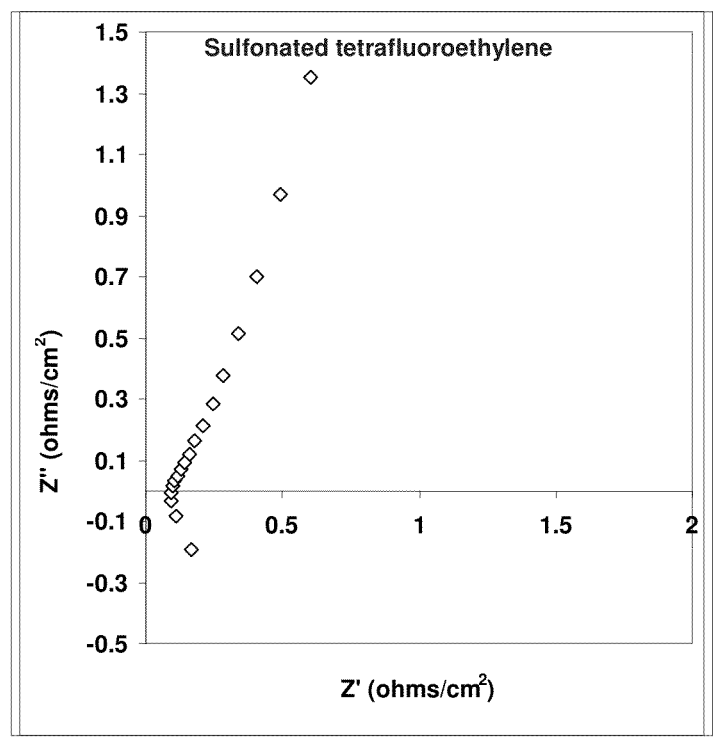

From the impedance spectra, the ionic conductivity of the membrane is obtained (e.g. protonic membrane) FIG. 5.

The conductivity $\sigma_m$ is obtained by determining the impedance modulus at the zero phase shift (side of high frequencies) using the following equation.

$$\sigma_m = \frac{d_m}{A \cdot |Z_m|_{\alpha=0}} \quad \text{Equation (8)}$$

where $d_m$ is the membrane thickness, A is the contact area of the membrane/electrode and $|Z_m|_{\alpha=0}$ is the modulus of the impedance at zero phase shift (FIG. 5).

Figure 6:
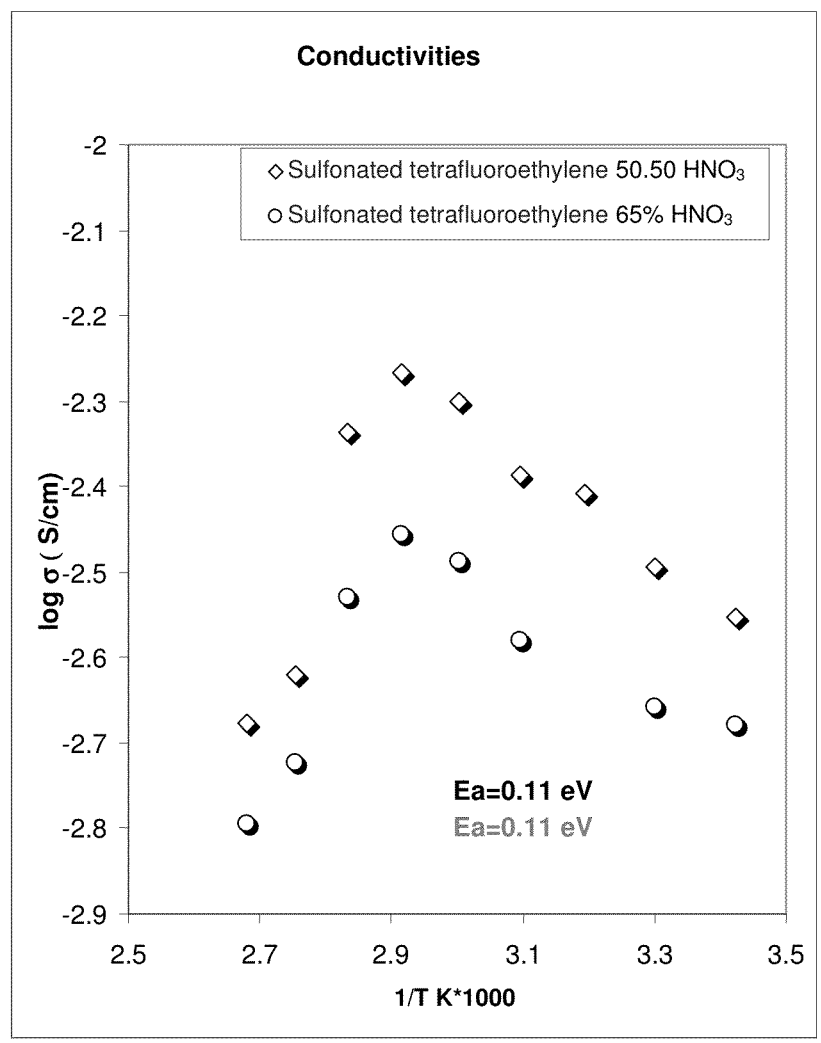
FIG. 6 shows the results obtained by the conductivity cell with hydrogen selective electrodes in a sulfonated tetrafluoroethylene copolymer membrane with protonic conductivity as a function of temperature.

The results obtained in a membrane made of sulfonated tetrafluoroethylene copolymer with proton conductivity are shown in FIG. 6.

APPLICATION EXAMPLES OF THE INVENTION AND COMPARISON TO OTHER METHODS AND MEASUREMENT DEVICES

In these cases a membrane commercially known (NAFION® 117) because of its performance can be taken as a reference.

Example 1

Conductivity measurements ($\sigma$ in S cm$^{-1}$) of sulfonated tetrafluoroethylene copolymer (Nafion®) activated in different solutions and under different atmospheres for the invention cell is shown in Table 1.

TABLE 1

| Conductivity measurements (S cm$^{-1}$) of invented modular cell. | | | |
|---|---|---|---|
| Solution to activate Nafion ® | H$_2$ | O$_2$ | H$_2$O (liquid) |
| H$_2$O$_2$ at 5% | 0.047 | 0.066 | 0.058 |
| HNO$_3$ at 65% | 0.069 | 0.077 | 0.077 |
| H$_3$PO$_4$ at 6M | 0.066 | 0.061 | 0.053 |
| HNO$_3$ 50:50 vol. | 0.094 | 0.099 | 0.078 |

Example 2

In Table 2, the conductivity measurements obtained by the Van der Pauw's method are shown for comparison in accordance with reference *Electrochimica Acta* 48 (2003) 4175-4187.

TABLE 2

| Conductivity measurements obtained by the Van der Pauw's method (Electrochimica Acta 48 (2003) 4175-4187). | |
|---|---|
| Water content (% wt) in Nafion ® | $\sigma$ (S cm$^{-1}$) |
| 10 | 0.003 |
| 30 | 0.058 |
| 36 | 0.03 |
| 43 | 0.077 |
| 50 | 0.072 |
| 70 | 0.02 |

Example 3

Figure 7:
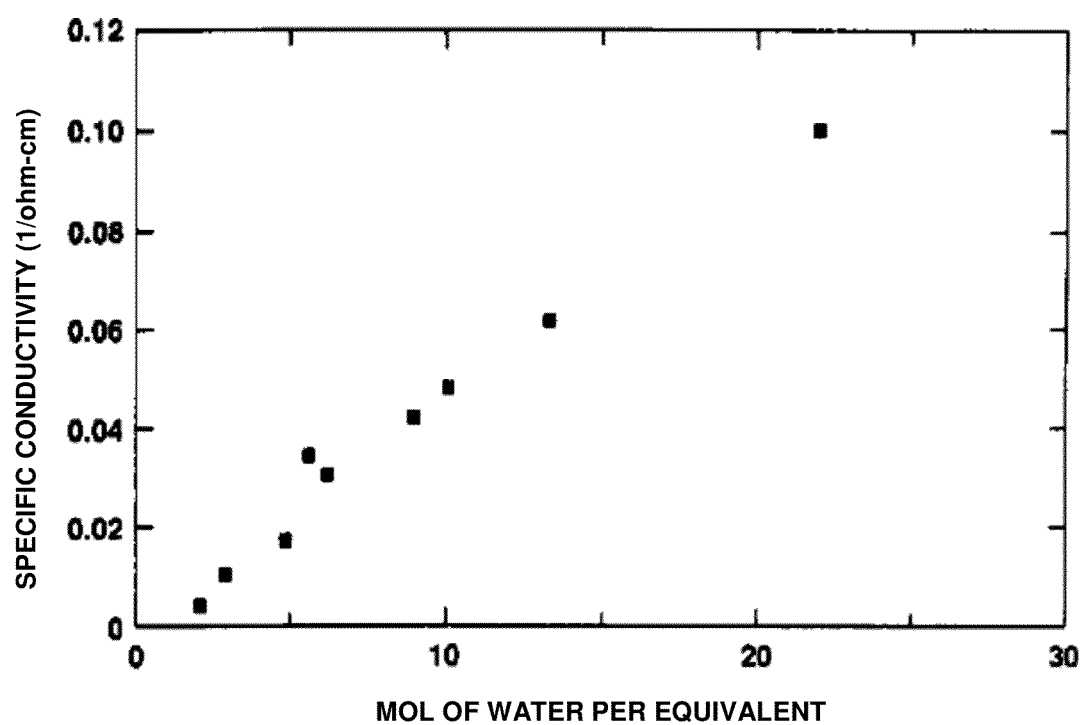
FIG. 7 shows a plot of specific conductivity vs. water mol per equivalent (taken from the J. Phys Chem. 1991, 95, 6040-6044)

In a conductivity cell in two electrode mode where the electric charge carriers flow on the membrane surface and not through it, as it is the case of invention cell, the graph is shown in accordance with reference *J. Phys. Chem.* 1991, 95, 6040-6044 (FIG. 7).

Example 4

Figure 8:
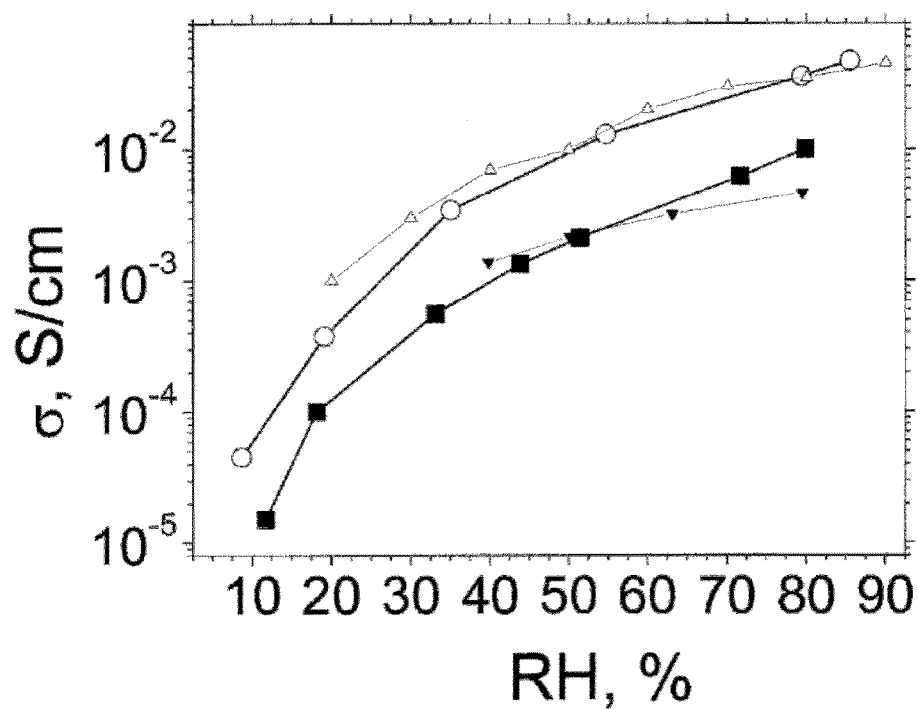
FIG. 8 shows the graph of σ vs. RH (taken from the patent application US2010/0109651).
where:
σ=specific conductivity
RH=relative humidity

In US 2010/0109651, another example of a conductivity cell in mode of two and four electrodes (FIG. 8) is shown. However, in contrast to the device of the invention, the charge carriers flow on the membrane surface and not through it, as it is the case for the cell of the present invention.

The examples above show ionic conductivity slightly higher than those obtained in the cell of the present invention. This is derived from the ohmic loss in the actual system because of the presence of "neck bottle" in Nafion®, points which are opened and closed as a function of water content in the bulk sample, which many times does not reach to humidify the internal surface membrane. This can produce distorted results because, in the other systems, charge carriers flow superficially where water greatly humidified the surface, which results in a membrane with a high ionic conductivity. However, when this membrane is subjected to real working conditions, there will be a great decay in the cell performance, as is the case of fuel cells.

What is claimed is:

1. A modular device for measuring ionic, electronic or mixed conductivity of polymeric, ceramics and composites membranes, which permits the simulation of working conditions of different types of membranes such as those used in fuel cells, batteries, pseudo-capacitors and sensors in their working environment, and operating with either gases or liquids, the device comprising:
   two aluminum plates each containing two compartments, each compartment having an electric heating element incorporated therein;
   a recess in one of the aluminum plates receiving a thermocouple;
   two fiberglass or glass seals provided on the plates;
   two current collectors of stainless steel;
   a first conductive mesh of graphite surrounded by a first polymeric insulation material that can endure temperatures up to 300° C.;
   a second conductive mesh of graphite surrounded by a second polymeric insulation material that can endure temperatures up to 300° C.; and
   a polymer, ceramic or mixed membrane removably positioned between the first and second graphite meshes.

2. A modular device for measuring ionic, electronic or mixed conductivity for polymeric, ceramic and composite membranes in accordance with claim 1, wherein the device is provided with an input hole and an output hole in each of the aluminum plates, where the input and output holes are aligned, respectively, to allow the input and output of fluids.

3. A modular device for measuring ionic, electronic or mixed conductivity for polymeric, ceramic and composite membranes in accordance with claim 2, wherein the aluminum plates each have one face minor polished to avoid fluid leaks, each of the compartments are disposed in an upper part of the respective plate, and each of the plates include a hole for the thermocouple wherein the thermocouple is a type K or type R thermocouple.

4. A modular device for measuring ionic, electronic or mixed conductivity for polymeric, ceramic and composite membranes in accordance with claim 3, wherein the thermocouple and the electric heating elements are connected to a temperature controller.

5. A modular device for measuring ionic, electronic or mixed conductivity for polymeric, ceramic and composite membranes in accordance with claim 4, wherein the fluid input holes are connected to a gas or liquid supply, which may be the same source for both inputs or two sources of different gases/liquids or different solutions.

6. A modular device for measuring ionic, electronic or mixed conductivity for polymeric, ceramic and composite membranes in accordance with claim 5, wherein input gases are wetted by a humidifier.

7. A modular device for measuring ionic, electronic or mixed conductivity for polymeric, ceramic and composite membranes in accordance with claim 6, wherein the device is operatively connected to a flow and pressure controller that can be automated by an external computer or manually controlled.

8. A modular device for measuring the ionic, electronic or mixed conductivity for polymeric, ceramic and composite membranes in accordance with claim 7, wherein the current collectors are connected to an impedance spectrometer.

9. A modular device for measuring the ionic, electronic or mixed conductivity for polymeric, ceramic and composite membranes in accordance with claim 8, wherein the aluminum plates, current collectors and membrane to be analyzed are aligned.

10. A modular device for measuring the ionic, electronic or mixed conductivity for polymeric, ceramic and composite membranes in accordance with claim 9, wherein four screws are used to fasten, fix, align, and center the modules to avoid leaks and losses of ohmic type.

11. A modular device for measuring the ionic, electronic or mixed conductivity for polymeric, ceramic and composite membranes in accordance with claim 10, wherein the alignment of the aluminum plates, current collectors and membrane allows the sealing and connection between the modules and avoids gas leaks.

12. A modular device for measuring the ionic, electronic or mixed conductivity for polymeric, ceramic and composite membranes in accordance with claim 11, wherein the placement of the polymer, ceramic or mixed membrane symmetrically divides the conductivity cell into two separated compartments so that the exchange of fluids from one compartment to the other can only be done through the membrane.

13. A modular device for measuring the ionic, electronic or mixed conductivity for polymeric, ceramic and composite membranes in accordance with claim 12, wherein the modular arrangement and electrode preparation permit material selectivity and allow for the flow of charge carriers within the membrane to be identified.

14. A modular device for measuring the ionic, electronic or mixed conductivity for polymeric, ceramic and composite membranes in accordance with claim 1, wherein the ionic electronic, or mixed conductivity is measured by the two electrodes in a direction perpendicular to a surface of the polymer, ceramic or composite membrane and in a direction perpendicular to a plane of the first and second conductive meshes.

15. A modular device for measuring ionic, electronic or mixed conductivity of polymeric, ceramics and composites membranes, wherein the ionic, electronic or the mixed conductivity is measured by two electrodes in a direction perpendicular to a surface of polymer, ceramic or composite membrane, the device comprising:
  a) two aluminum plates each containing two compartments having two electric heating elements incorporated therein;
  b) the two aluminum plates each having two orifices, the two orifices being a fluid inlet and a fluid outlet;
  c) the two compartments are configured to be filled with a liquid or gaseous fluid;
  d) the two electrodes, each having a square, flat surface, are separated by a membrane;
  e) a first current collector comprising stainless steel, which is in contact with a first electrode having a square-shaped flat surface, the first electrode being in contact with a surface of the membrane, through which passes an alternating current and voltage at different frequencies;
  f) a second current collector comprising stainless steel, which is in contact with a second electrode having a square-shaped flat surface, the second electrode being in contact with the membrane surface, whereby passing an alternating current and voltage at different frequencies;
  g) a recess in one of the aluminum plates receiving a thermocouple;
  h) two O-ring seals each having a shaped frame to prevent the escape of fluids from the device, the O-ring seals separating and isolating the two aluminum plates from a core of a conductivity cell;
  i) a first removable conductive mesh of graphite surrounded by a first polymeric, fiberglass or glass insulation material that is configured to endure temperatures up to 300° C.; and
  j) a second removable conductive mesh of graphite surrounded by a second polymeric, fiberglass or glass insulation material that is configured to endure temperatures up to 300° C.; wherein
  k) the polymer, ceramic or mixed membrane is removably positioned between the first and second graphite meshes.

16. A modular device for measuring ionic, electronic or mixed conductivity of polymeric, ceramics and composites membranes, which permits the simulation of working conditions of different types of membranes such as those used in fuel cells, batteries, pseudo-capacitors and sensors in their working environment, and operating with either gases or liquids, the device comprising:
  two aluminum plates each containing two compartments, each compartment having an electric heating element incorporated therein;
  a recess in one of the aluminum plates receiving a thermocouple;
  two fiberglass or glass seals provided on the plates;
  two current collectors of stainless steel;
  a conductive mesh surrounded by a polymeric insulation material that can endure temperatures up to 300° C.; and
  a polymer, ceramic or mixed membrane removably positioned adjacent to the conductive mesh.

17. A modular device for measuring the ionic, electronic or mixed conductivity for polymeric, ceramic and composite membranes in accordance with claim 16, wherein the conductive mesh is a material selected from the group consisting of platinum, palladium, and gold to control the flow of charge carriers through the membrane.

18. A modular device for measuring ionic, electronic or mixed conductivity for polymeric, ceramic and composite membranes in accordance with claim 16, wherein the conductive mesh is a material selected from the group consisting of platinum, gold, and graphite mesh coated with conductive materials of ionic or electronic type, which allows selectivity toward the charge carriers in the membrane, or to block the flow of a certain charge carrier to observe the electronic flow in the membrane, or identify the mixed flow of the charge carriers.

* * * * *